United States Patent
Zardi

(10) Patent No.: US 7,585,473 B2
(45) Date of Patent: Sep. 8, 2009

(54) CARBAMATE CONDENSATION UNIT

(75) Inventor: Federico Zardi, Breganzona (CH)

(73) Assignee: Urea Casale S.A. (CH)

( * ) Notice: Subject to any disclaimer, the term of this patent is extended or adjusted under 35 U.S.C. 154(b) by 108 days.

(21) Appl. No.: 10/399,895

(22) PCT Filed: Oct. 1, 2001

(86) PCT No.: PCT/EP01/11325

§ 371 (c)(1),
(2), (4) Date: Aug. 25, 2003

(87) PCT Pub. No.: WO02/34382

PCT Pub. Date: May 2, 2002

(65) Prior Publication Data

US 2004/0028578 A1 Feb. 12, 2004

(30) Foreign Application Priority Data

Oct. 24, 2000 (EP) .................................. 00123047

(51) Int. Cl.
*B01J 19/00* (2006.01)
*C07C 273/04* (2006.01)
(52) U.S. Cl. .................. 422/197; 422/196; 422/202; 422/231; 422/234; 165/158; 564/67
(58) Field of Classification Search ............ 422/197, 422/227, 234
See application file for complete search history.

(56) References Cited

U.S. PATENT DOCUMENTS

| 2,386,681 A | * | 10/1945 | Hadden ............... 585/720 |
| 2,761,768 A | | 9/1956 | Diels et al. |
| 3,108,048 A | | 10/1963 | McDonald |
| 3,676,485 A | | 7/1972 | Lewis et al. |
| 3,927,982 A | | 12/1975 | Chapman et al. |
| 4,119,670 A | * | 10/1978 | Tsuchiya ............... 564/477 |
| 4,342,876 A | | 8/1982 | Klingman |
| 4,472,061 A | | 9/1984 | Mansour |
| 4,683,121 A | | 7/1987 | Goudriaan et al. |

FOREIGN PATENT DOCUMENTS

| DE | 2136399 A | * | 2/1973 |
| EP | 0 310 878 A1 | | 4/1989 |
| EP | 1 036 787 A1 | | 9/2000 |
| SU | 129643 | | 11/1959 |
| SU | 262836 | | 8/1967 |
| SU | 1389837 A1 | | 4/1988 |
| WO | WO 00/43358 | | 7/2000 |

OTHER PUBLICATIONS

Ullmann's Encyclopedia of Industrial Chemistry, 1992, vol. 85, p. 290.

* cited by examiner

*Primary Examiner*—Jennifer A Leung
(74) *Attorney, Agent, or Firm*—Akerman Senterfitt

(57) ABSTRACT

A carbamate condensation unit of the submerged type for synthesis urea production plants comprising a tube bundle for the condensation of gaseous compounds, is distinguished in that it further comprises a duct, structurally independent from the tube bundle, for the circulation of part of the condensed gaseous compounds inside the condensation unit.

2 Claims, 3 Drawing Sheets

CARBAMATE CONDENSATION UNIT

FIELD OF APPLICATION

The present invention relates to a carbamate condensation unit of the so-called submerged type, used in a plant for the production of synthesis urea from gaseous carbon dioxide and liquid ammonia.

PRIOR ART

In order to produce urea, the reactants, i.e. carbon dioxide and ammonia, are fed partially condensed in form of carbamate, in a synthesis reactor wherein the condensation of carbamate, an intermediate product of the synthesis, is carried out to an almost complete extent. Only a portion of the carbamate is then converted into urea in the reactor itself, by virtue of the chemical balances that characterize this conversion.

The remaining portion of unconverted carbamate, together with the unreacted ammonia, is then forced out of the reactor and at least partially recovered, by stripping, for example with $CO_2$, in form of gaseous ammonia and carbon dioxide by per se known processes.

These gaseous substances must then be partially condensed, thus obtaining their conversion into liquid carbamate that is then recycled to the synthesis reactor.

As known, in a plant for urea production, it is required to convert through condensation into carbamate part of the reactants and of the intermediate products that, unconverted into urea in the synthesis reactor, are recovered downstream thereof in form of gaseous ammonia and carbon dioxide.

In order to satisfy the aforesaid requirement, in EP-A-1 036 787 a condensation unit of the so-called submerged type has been proposed, comprising a cylindrical shell inside which is supported a tube bundle, wherein the tubes are straight and in heat exchange relationship with a suitable coolant.

In the tube bundle, ammonia and carbon dioxide condensation takes place, together with their reaction to form carbamate.

Although advantageous as far as some aspects thereof are concerned, the condensation unit exhibits a remarkable drawback that will be described hereinbelow.

In fact, only a part, although a major part, of the tubes of the tube bundle are used for the conversion into carbamate of the gaseous compounds flowing from a lower end to an upper end thereof. The remaining portion of the tube bundle must instead be used for the recycle of a portion of the condensed gaseous compounds from the upper end to the lower end thereof. The latter in order to allow a natural circulation of the liquid phase inside the condenser so as to increase the heat exchange coefficient of the apparatus.

Accordingly, given a tube bundle of predetermined size, the yield is strictly bound to the only part thereof intended for the condensation.

SUMMARY OF THE INVENTION

The object of the present invention is to provide a high efficiency condensation unit, wherein, at equal size of the tube bundle, the yield in condensed gaseous compounds is remarkably increased with respect to the teaching of the prior art.

This object is achieved by a carbamate condensation unit of the submerged type for synthesis urea production plants, comprising:

a substantially cylindrical shell, closed at the opposed ends thereof by an upper and a lower bottom, respectively, defining an intermediate portion, an upper portion and a lower portion of the condensation unit;

a tube bundle for the condensation of gaseous compounds, fitted into the intermediate portion of the condensation unit and in fluid communication with the upper portion and the lower portion;

characterized in that it comprises:

a duct, structurally independent from the tube bundle, in fluid communication with the upper and lower portions, for the circulation of part of the condensed gaseous compounds.

Preferably, the gaseous compounds $NH_3$ and $CO_2$ to be condensed coming from a stripping unit downstream the synthesis reactor, a flow comprising carbamate in aqueous solution coming from a urea recovery section, and optionally a solution comprising urea coming from the synthesis reactor and feed liquid ammonia, are fed in the lower portion of the condensation unit through respective dedicated openings in the lower bottom.

The condensed gaseous compounds are instead made exit from the condensation unit through at least an opening in the upper bottom in fluid communication with the upper portion of the condensation unit.

Thanks to the present invention, the whole tube bundle is used in order to carry out the condensation step. In fact, the presence of a duct structurally independent from the tube bundle, in fluid communication with the upper and lower portions of the condensation unit, allows advantageously the circulation of the carbamate outside the tube bundle.

As the tube bundle is exclusively used to carry out the condensation, the present invention allows advantageously increasing the yield of such condensation, the size of the tube bundle being the same.

Further features and advantages of the present invention will appear more clearly from the following non-limiting description of an embodiment thereof, made with reference to the attached drawings.

DETAILED DESCRIPTION OF THE DRAWINGS

Figure 1:
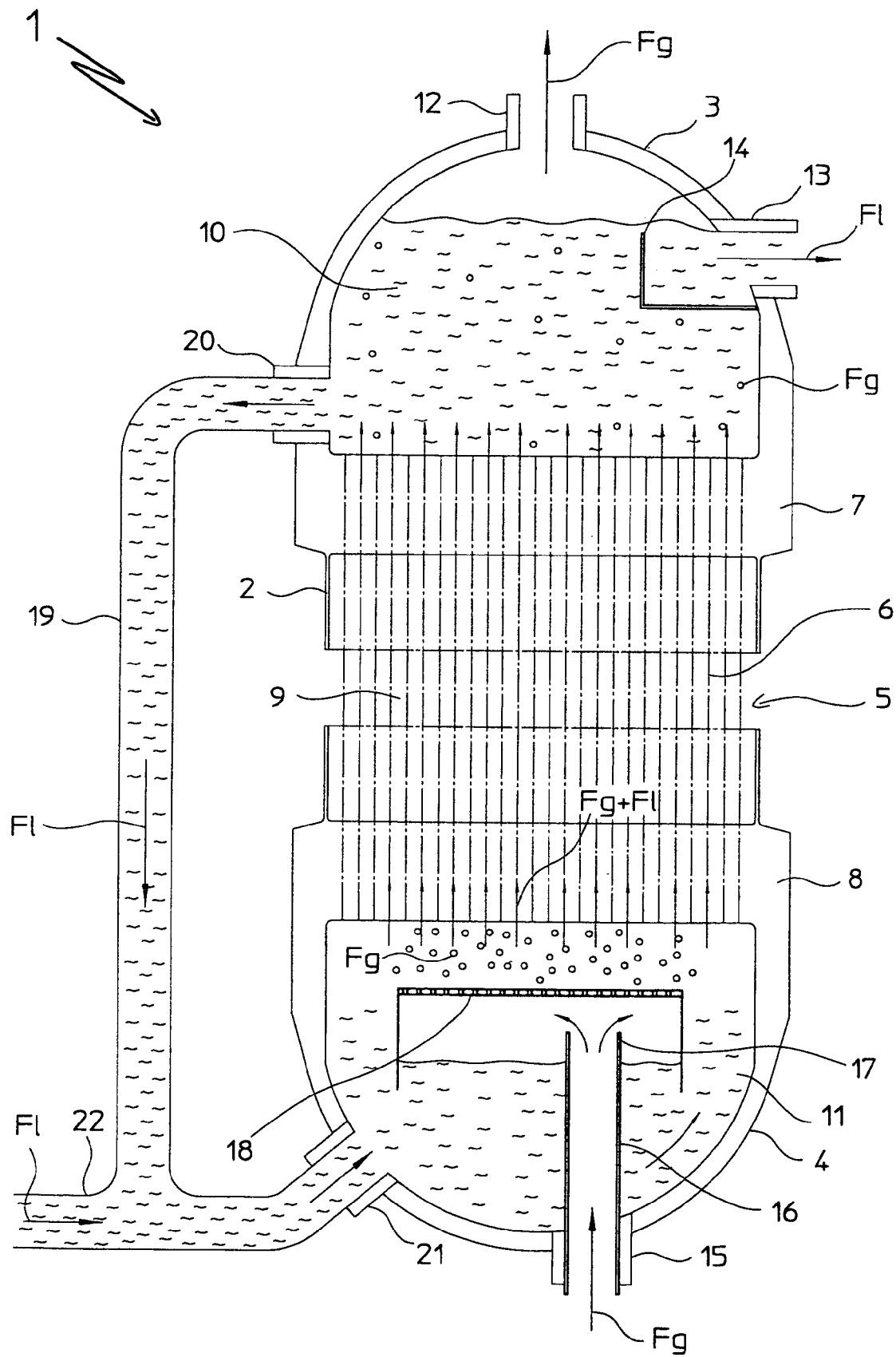
FIG. 1 shows a schematic view in longitudinal section of a condensation unit obtained according to the present invention.

With reference to FIG. 1, with 1 is globally indicated a condensation unit according to the present invention comprising a cylindrical shell 2 closed at the opposed ends by an upper bottom 3 and a lower bottom 4, respectively.

In the shell 2 a tube bundle 5 is supported having a predetermined size, i.e. having a predetermined number of straight tubes 6 of predetermined length and diameter, said straight tubes 6 being supported by opposed upper and lower tube plates 7, 8, respectively. Said plates 7 and 8 separate the shell 2, which defines an intermediate portion 9 of the condensation unit, from the bottoms 3 and 4, which define an upper portion 10 and a lower portion 11 of the condensation unit, respectively.

Said portions 10 and 11 are reciprocally in fluid communication through the plurality of straight tubes 6 of the tube bundle 5.

It shall be noted that said tube bundle 5 is in heat exchange relationship with a coolant, for example water, flowing outside the tubes 6 (shell side) and fed into the condensation unit and exiting therefrom through suitable openings and connecting means that are not shown as per se conventional.

The upper portion 10 of the condensation unit is provided with a first gas discharge opening 12, formed in the upper bottom 3 and with a second opening 13 formed in the side part of the portion itself.

In said portion 10, and in proximity to said second opening 13, an overflow device 14 is provided, which is schematically illustrated by a baffle.

The lower portion 11 is provided with a first opening 15 to which passes a first duct 16 fastened thereto, for feeding the gases to be condensed, as will be clear in the following description.

Said first duct 16 has a free end 17, located inside a gas distribution chamber 18, supported in a conventional manner inside said lower portion 11 of the condensation unit.

According to the present invention, a duct 19, extending outside the shell 2, is in fluid communication on one side with the upper portion 10 of the condensation unit and on the other side with the lower portion 11 through openings 20 and 21, respectively.

Said duct 19 is structurally independent from the tube bundle 5 and furthermore is in fluid communication with a second feeding duct 22.

The functional features according to the present invention will be now indicated by making reference to the figures. In these figures, Fg and Fl generally indicate the flows of the gaseous phase and of the liquid phase inside the condensation unit 1, respectively.

With reference to FIG. 1, the volume of the condensation unit 1, schematically illustrated when in regular operation, is entirely taken up by an aqueous solution comprising carbamate, ammonia and optionally urea and by a mixture comprising ammonia, carbon dioxide and water in the form of vapors.

Said substances in a vapor phase come from a stripping unit (not shown) downstream a synthesis reactor (not shown) for the decomposition of carbamate and the ammonia and carbon dioxide stripping from the urea solution coming from the synthesis reactor. These substances are fed into the condensation unit by the above said first feeding duct 16 and distributed through the gas distribution chamber 18 inside the lower portion 11, near a lower end of the tubes 6 of the tube bundle 5.

This implies a mixing of said gaseous compounds with said aqueous solution that is already present in the lower portion 11.

From the lower portion 11, the gaseous compounds and the aqueous solution mixed together flow inside the straight tubes 6 of the tube bundle 5.

Inside said tube 6, ammonia, carbon dioxide and water condensate and ammonia reacts with carbon dioxide, thus forming carbamate.

This carbamate is added to the carbamate already present in the aqueous solution inside the condensation unit 1, obtaining in this way, at the outlet of the tubes 6, one carbamate solution possibly comprising also urea.

The carbamate solution flows in the upper portion 10, wherein a first part thereof is recycled to the lower portion 11 through the duct 19, and a second part thereof exits the unit 1 through the opening 13 with a flow regulated by the overflow device 14. The portion of solution exiting the unit 1 through the opening 13 is then sent to the synthesis reactor for the conversion into urea of the carbamate and ammonia therein contained.

It shall be noted that the duct 19 provides the circulation of the aqueous solution inside the condensation unit 1, in particular from the upper portion 10 of the condensation unit to its lower portion 11.

Said circulation guarantees that the straight tubes 6 are always full of solution and contain a constant amount thereof. Further on, it allows an optimal crossing speed through the tubes 6 to be maintained by the liquid phase to all advantage of the heat exchange between said liquid phase and the coolant flowing outside the tubes 6, and therefore of a more effective condensation of the gaseous compounds.

A part of the aqueous solution flowing inside the condensation unit 1 is supplied from outside through a flow comprising carbamate in aqueous solution coming from a urea recovery section (not shown) and possibly unreacted substances coming from the synthesis reactor and feed liquid ammonia. Said flow is fed to the lower portion 11 of the shell 2 through a duct 22 that ends up into the duct 19 in order to be added to the recycle aqueous solution. In this way no further openings shall be provided into the lower bottom 4 of the condensation unit 1.

Once introduced in the lower portion 11 of the condensation unit 1, the aqueous solution mixes up with the gaseous compounds coming out of the distribution chamber 18 and as described above is made circulating within the condensation unit 1.

Should any gaseous substance be still present in the upper portion 10, they will be vented from the condensation unit 1 through the opening 12 obtained in the upper bottom 3.

The synthesis reactor, the stripping unit and the condensation unit 1 are all part of the so-called high-pressure synthesis loop of plant for the industrial production of urea. Such apparatuses do in fact operate substantially at the same pressure and are connected the one to the other in order to make possible the separation and recycle to the synthesis reactor of at least a portion of the unreacted substances contained in the urea solution coming out therefrom.

The above described condensation unit 1 is subject to modifications and changes.

Figure 2:
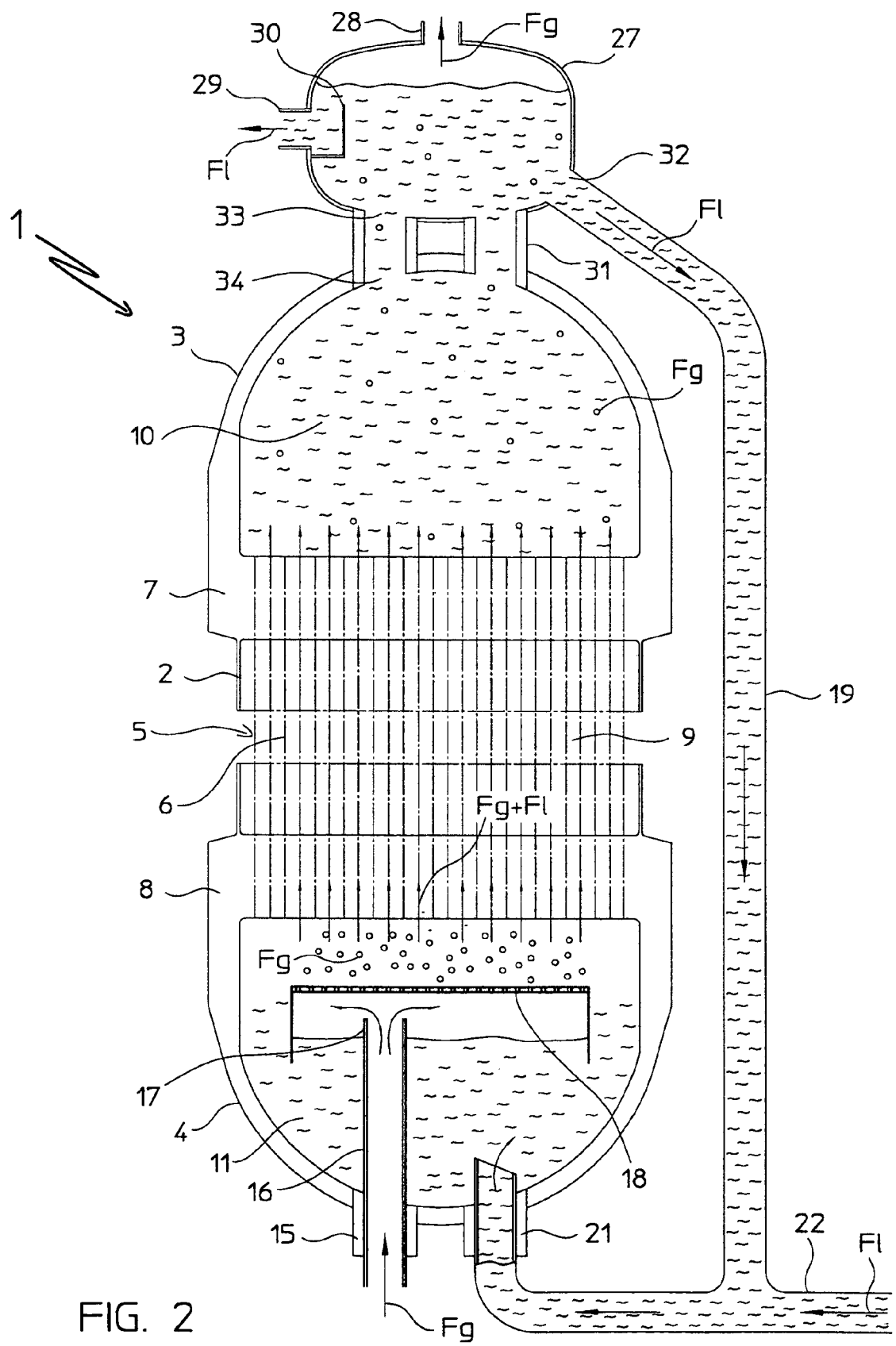
FIG. 2 shows a schematic view in longitudinal section of a condensation unit according to an alternative embodiment of the present invention.

Thus, an alternative embodiment of the invention is for example shown with reference to FIG. 2.

In this figure, the details of the condensation unit 1 that are structurally and functionally equivalent to those illustrated in FIG. 1 will be indicated with the same reference numbers and will not be described any more.

The condensation unit 1 comprises a tank 27 arranged externally to the upper bottom 3.

The tank 27 comprises at least a first lower opening 33 (two in the example of FIG. 2), a second lower opening 32 in fluid communication with the duct 19, a third gas discharge opening 28 in the upper portion and, on a side, a fourth opening 29.

In turn, the upper bottom 3 of the condensation unit 1 has at least an upper opening 34 to which a nozzle 31 is associated (two in the example of FIG. 2).

In FIG. 2, the tank 27 is in fluid communication with the upper portion 10 of the unit 1 through the lower openings 33 fixed to the corresponding nozzles 31 of the upper bottom 3.

In proximity to the fourth opening 29 an overflow device 30 is provided, which is schematically illustrated by a baffle.

The functional characteristics according to the present alternative embodiment of the invention will be now described with reference to FIG. 2.

According to this embodiment, the aqueous solution flowing from the tube bundle 5 to the upper portion 10 is fed into the tank 27 through the openings 34, the nozzles 31 and the openings 33.

A first portion of the aqueous solution collected inside the tank 27 is recycled to the lower portion 11 of the unit 1 through the opening 32 and then the duct 19, whereas a second portion comes out of the condensation unit 1 through the opening 29 to be fed to the urea synthesis reactor. The overflow device 30 regulates the outlet flow from the opening 29.

Finally, should any gaseous substance be still present in the tank 27, it will be vented from unit 1 through the opening 28.

This alternative embodiment is particularly advantageous for the revamping of pre-existing condensation units, for example condensation units of the film type.

In said units, the liquid phase is made flow for gravity inside the tubes of a tube bundle as a film of liquid in co-current with the gaseous compounds to be condensed.

In the preexisting condensation units it is not possible neither economically convenient to make structural modifications to the same, in particular to the shell.

Advantageously, thanks to this embodiment of the invention, a tank 27 is provided to set in fluid communication the upper portion 10 of the condensation unit 1 with the lower portion 11 thereof, for the circulation of the aqueous solution inside this unit without the need of intervening onto the existing structure of the shell 2 and of the bottoms 3 and 4.

Figure 3:
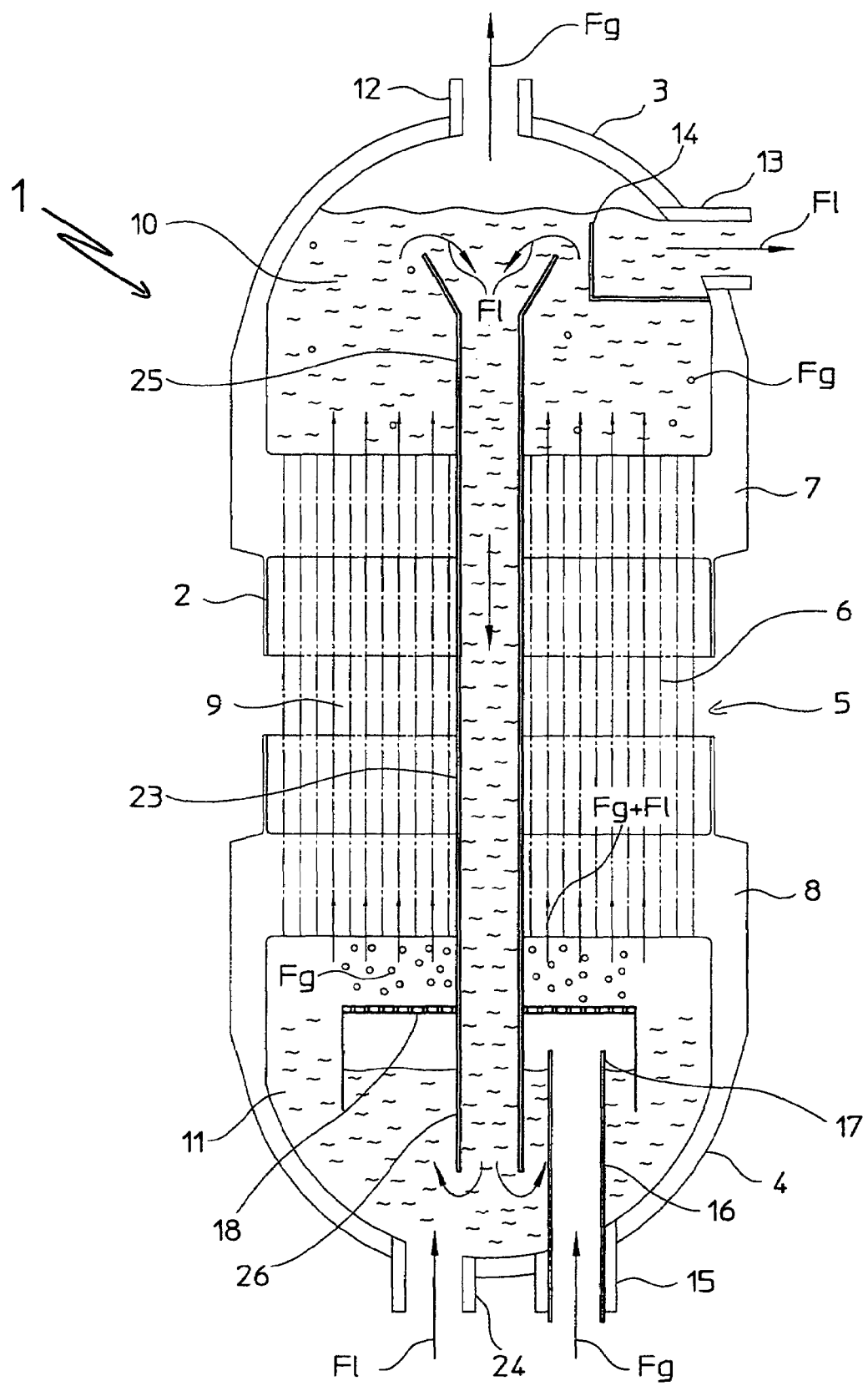
FIG. 3 shows schematic view in longitudinal section of a condensation unit according to a further embodiment of the present invention.

With reference to FIG. 3, a further embodiment of the invention is shown.

In this figure, the details of the condensation unit 1 that are structurally and functionally equivalent to those illustrated in FIG. 1 will be indicated with the same reference numbers and will not be described any more.

As an alternative to the external duct 19 represented in the previous figures, this embodiment provides the arrangement of a duct 23, structurally independent from the tube bundle 5, which extends internally to the condensation unit 1 through the shell 2 and is supported by the tube plates 7 and 8. The duct 23 is in fluid communication with the upper and lower portions 10 and 11 through respective upper and lower ends 25, 26 for the circulation of the condensed gaseous compounds within the condensation unit 1.

In the example of FIG. 3, the duct 23 is arranged coaxially to the shell 2 and is extended lengthwise from the upper portion 10 near the baffle 14 to the lower portion 11 in proximity to the lower bottom 4.

A second opening in the lower bottom 4 of the condensation unit 1 is indicated with 24. This opening is for the feed into the lower portion 11 of the condensation unit 1 of the flow comprising carbamate in aqueous solution coming from the urea recovery section and optionally a solution comprising urea coming from the synthesis reactor and feed liquid ammonia.

According to this embodiment, beside the yield increase in the condensation unit 1 with respect to the prior art, an advantageous reduction of the overall volume of the condensation unit itself is achieved. Further on, the costs for manufacturing such a unit are lower than those for manufacturing the units according to the previously described embodiments of the invention, because of the absence of an external high-pressure duct.

In fact, the duct 23 is advantageously arranged within the condensation unit 1 in order to carry out the circulation of the aqueous solution inside it.

The invention claimed is:

1. A submerged carbamate condensation unit for synthesis urea production plants, comprising:
   a substantially cylindrical shell, closed at the opposed ends thereof by an upper and a lower bottom, respectively, defining an intermediate portion, an upper portion and a lower portion of the condensation unit;
   a tube bundle for the condensation of gaseous compounds, fitted into said intermediate portion of the condensation unit, in fluid communication with said upper portion and said lower portion and comprising an upper and a lower tube plate, respectively, and a plurality of tubes supported by said upper and lower tube plates;
   a first duct extended in said lower portion below said tube bundle for feeding said gaseous compounds to be condensed and having a free end located inside a gas distribution chamber supported inside said lower portion of the condensation unit;
   discharge openings provided in said upper portion for discharging outside the condensation unit uncondensed gaseous compounds and condensed gaseous compounds, respectively;
   a second duct, structurally independent from said tube bundle and said discharge openings, in fluid communication with said upper and lower portions for the circulation of part of said condensed gaseous compounds, wherein said second duct is external to said shell; and
   a tank associated to said upper bottom and in fluid communication with said upper portion and said second duct external to said shell, said discharge openings being provided in said tank.

2. The carbamate condensation unit according to claim 1, wherein said second duct is in communication with said lower portion via an opening that is positioned lower than said free end of said first duct supplying said gaseous compounds.

* * * * *